United States Patent
Bressler et al.

(10) Patent No.: US 7,112,190 B2
(45) Date of Patent: Sep. 26, 2006

(54) BLOOD COLLECTION DEVICE

(75) Inventors: Peter Bressler, Philadelphia, PA (US); Bradley M. Wilkinson, North Haledon, NJ (US); Stefanie Livanos, Bethlehem, PA (US); Kirk D. Swenson, North Caldwell, NJ (US); Charles G. Hwang, Ridgewood, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 0 days.

(21) Appl. No.: 10/392,254

(22) Filed: Mar. 17, 2003

(65) Prior Publication Data

US 2003/0181874 A1    Sep. 25, 2003

Related U.S. Application Data

(60) Provisional application No. 60/366,367, filed on Mar. 20, 2002.

(51) Int. Cl.
*A61M 5/00* (2006.01)
(52) U.S. Cl. .................................... 604/263
(58) Field of Classification Search ............... 604/192, 604/187, 110, 263, 197, 162, 177, 198, 164.01; 128/819; 600/573
See application file for complete search history.

(56) References Cited

U.S. PATENT DOCUMENTS

| | | | |
|---|---|---|---|
| 4,941,881 A | 7/1990 | Masters et al. | |
| 4,966,591 A | 10/1990 | Yuen | |
| 5,030,212 A | 7/1991 | Rose | |
| 5,112,311 A | 5/1992 | Utterberg et al. | |
| 5,120,320 A | 6/1992 | Fayngold | |
| 5,147,319 A * | 9/1992 | Ishikawa et al. | 604/174 |
| 5,188,611 A | 2/1993 | Orgain | |
| 5,266,072 A | 11/1993 | Utterberg et al. | |
| 5,290,264 A | 3/1994 | Utterberg | |
| 5,509,907 A | 4/1996 | Bevilacqua | |
| 5,584,816 A | 12/1996 | Gyure et al. | |
| 5,669,889 A | 9/1997 | Gyure et al. | |
| 5,681,295 A | 10/1997 | Gyure et al. | |
| 5,693,022 A | 12/1997 | Haynes | |
| 5,772,638 A * | 6/1998 | Utterberg et al. | 604/263 |
| 5,891,103 A | 4/1999 | Burns | |
| 5,951,525 A * | 9/1999 | Thorne et al. | 604/198 |
| RE37,110 E | 3/2001 | Hollister | |
| RE37,252 E | 7/2001 | Hollister | |
| 6,254,577 B1 | 7/2001 | Huet | |
| 6,309,376 B1 | 10/2001 | Alesi | |
| 2001/0039401 A1 | 11/2001 | Ferguson et al. | |

FOREIGN PATENT DOCUMENTS

JP    8-206195    8/1996

* cited by examiner

*Primary Examiner*—Kevin Sirmons
(74) *Attorney, Agent, or Firm*—Mark J. Schildkraut

(57) ABSTRACT

A safety needle assembly has a needle hub and a needle cannula projecting from the hub. Wings project transversely from the hub to facilitate manipulation and positioning of the needle assembly. A shield is hingedly attached to the needle hub and can be rotated from a first position where the needle cannula is exposed to a second position where the needle cannula is shielded. At least one latch may be disposed on the shield for secure locked engagement with the hub, the wings and/or the tubing extending from the hub. A spring may also be provided for propelling the shield into the second position.

12 Claims, 14 Drawing Sheets

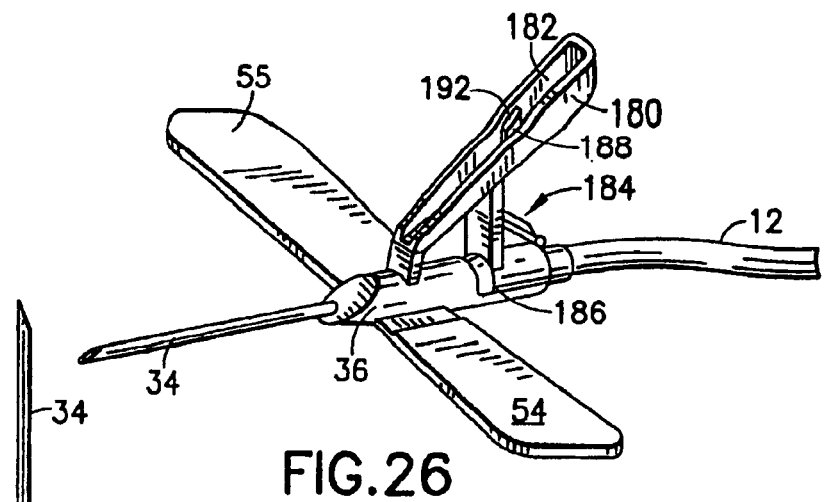
FIG.26
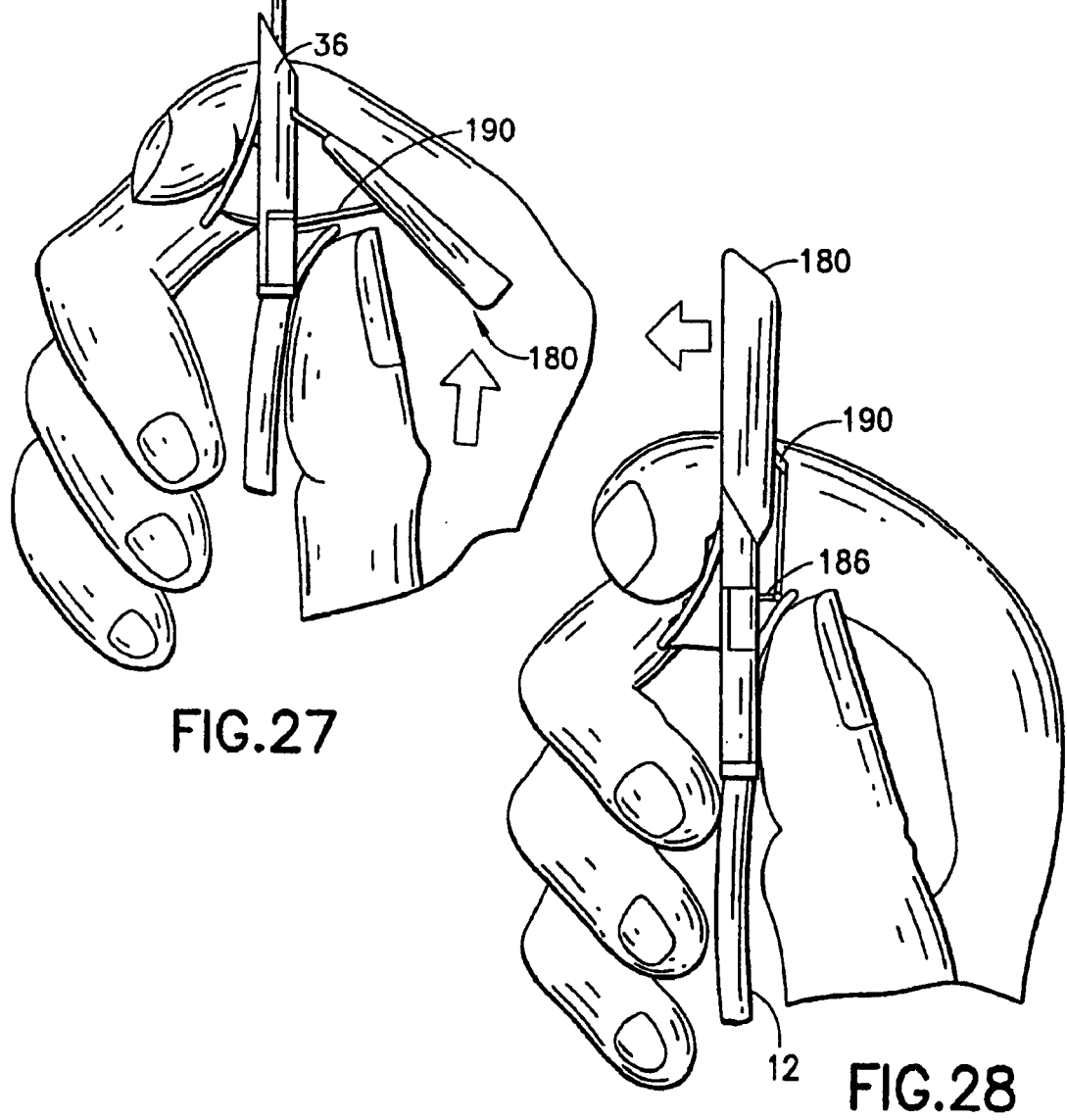
FIG.27
FIG.28

BLOOD COLLECTION DEVICE

RELATED APPLICATION

This application is a non-provisional of U.S. Provisional Patent Appl. No. 60/366,367, filed Mar. 20, 2002.

FIELD OF THE INVENTION

The invention relates to a medical apparatus with a needle for fluid collection or infusion and with a hinged shield for safely enclosing the medical apparatus.

BACKGROUND OF THE INVENTION

Disposable medical devices having piercing elements for administering a medication or withdrawing a fluid, such as hypodermic needles, blood collecting needles, fluid handling needles and assemblies thereof, require safe and convenient handling. The piercing elements include, for example, pointed needle cannula or blunt ended cannula.

The above-described medical devices often include a pair of flexible plastic wings mounted to or near the needle hub. The wings can be folded into face-to-face engagement with one another, and hence define a convenient handle for gripping and manipulating the needle cannula. The wings also can be rotated away from one another and can be taped into face-to-face contact with the skin of the patient.

Accidental sticks with a needle cannula can be painful and can transmit disease. As a result, most needle assemblies are employed with rigid means for enclosing the needle cannula both prior to use and after use. Protection prior to use typically is achieved by a rigid plastic tube that has a proximal end frictionally mounted to the needle hub and a distal end that extends beyond the distal end of the needle cannula. The plastic tube is removed and discarded immediately prior to use of the needle cannula. Protection after use of the needle cannula typically is achieved by a shield that can be moved relative to the needle cannula from a first position where the needle is exposed to a second position where the needle cannula is safely within the shield. Shields of this type typically include means for releasably holding the shield in its first position and for holding the shield more securely in its second position. The retention of the shield in its second position should prevent any accidental re-exposure of the used needle cannula and preferably should prevent or substantially complicate an intentional attempt to reuse the needle cannula.

A demand exists for a medical device that provides secure shielding and an easy operation.

SUMMARY OF THE INVENTION

The invention is directed to a fluid collection or infusion set. The fluid collection or infusion set comprises a length of flexible plastic tubing with opposite proximal and distal ends and a passage extending between the ends. A fitting is connected securely to the proximal end of the flexible plastic tubing.

The fluid collection or infusion set further comprises a safety needle assembly secured to the distal end of the flexible tubing. The needle assembly includes a needle hub with a proximal end, a distal end and a passage extending between the ends. Portions of the passage adjacent the proximal end of the hub are configured for secure engagement with the distal end of the flexible plastic tubing.

The needle assembly further includes a needle cannula having opposite proximal and distal ends and a lumen extending between the ends. The proximal end of the needle cannula is affixed securely to the distal end of the needle hub so that the lumen through the needle cannula communicates with the passage through the needle hub and with the passage through the flexible tubing. The needle assembly may further include a needle protector removably mounted over the needle cannula and extending sufficiently to cover the distal end of the needle cannula.

The needle assembly further includes a pair of flexible wings that extend transversely from the needle hub. The wings may be formed separately from the needle hub and may be mounted to a portion of the needle hub. Thus, the needle hub may be formed from a first plastic material selected for rigidity, while the wings may be formed from a second plastic or elastomeric material selected for flexibility. Alternatively, the wings may be unitary with the hub, and thinned portions of the wings adjacent the hub may function as hinges.

The needle assembly may further comprise a safety shield hingedly connected to the needle hub for rotation from a first position where the needle cannula is exposed for use to a second position where the needle cannula is safely enclosed within the shield. The shield may comprise means for permanently locking the shield in the second position. The locking means may comprise at least one resiliently deflectable cannula finger lock that snaps into engagement with the needle cannula when the shield reaches the second position. Alternatively, or additionally, the locking means may comprise means for lockingly engaging the needle hub and/or the plastic tubing.

The locking means may comprise a first locking means for releasably holding the shield in the first position and a second locking means for permanently holding the shield in the second position. The first locking means functions to prevent the shield from interfering with normal usage of the needle assembly. The second locking means, however, permanently shields the needle cannula after use and substantially prevents intended or unintended re-exposure of the used needle cannula.

The shield may be hinged to rotate about an axis aligned orthogonal to the needle cannula. The axis of rotation of the shield may be substantially parallel to the wings when the wings are rotated into their substantially coplanar orientation on opposite respective sides of the hub. Alternatively, the axis of rotation of the shield may be aligned substantially normal to the wings when the wings are in their coplanar orientation and projecting from opposite lateral sides of the needle hub.

The needle assembly may further include biasing means for urging the shield into the second position. The biasing means may be formed unitarily with the hinged connection of the shield to the needle assembly. More particularly, the biasing means may be an over center hinge that initially biases the shield toward the first position. However, sufficient rotation of the shield will move the over center hinge into a position where the hinge urges the shield into the second position. Alternatively, the biasing means may comprise a separate spring having a first portion secured to the needle hub and a second portion secured to a location on the shield. The connections of the spring to the shield and the hub are spaced from the hinged connection between the shield to the hub.

The needle assembly may further include a dorsal fin that projects from the needle hub at a location spaced angularly from the wings. The dorsal fin can be used to facilitate digital manipulation of the needle assembly during a medical procedure. The dorsal fin may include or be connected to the shield. Thus, forces exerted on the dorsal fin after use can enable the shield to be moved from the first position to the second position.

BRIEF DESCRIPTION OF THE DRAWINGS

FIG. 26 is a perspective view of a safety needle assembly in accordance with a thirteenth embodiment of the invention with the shield in the open position.

FIG. 27 is a side elevational view of the safety needle assembly shown in FIG. 25 at the start of a shielding operation.

FIG. 28 is a side elevational view similar to FIG. 26, but showing the safety needle assembly after completion of shielding.

DETAILED DESCRIPTION OF THE INVENTION

Figure 1:
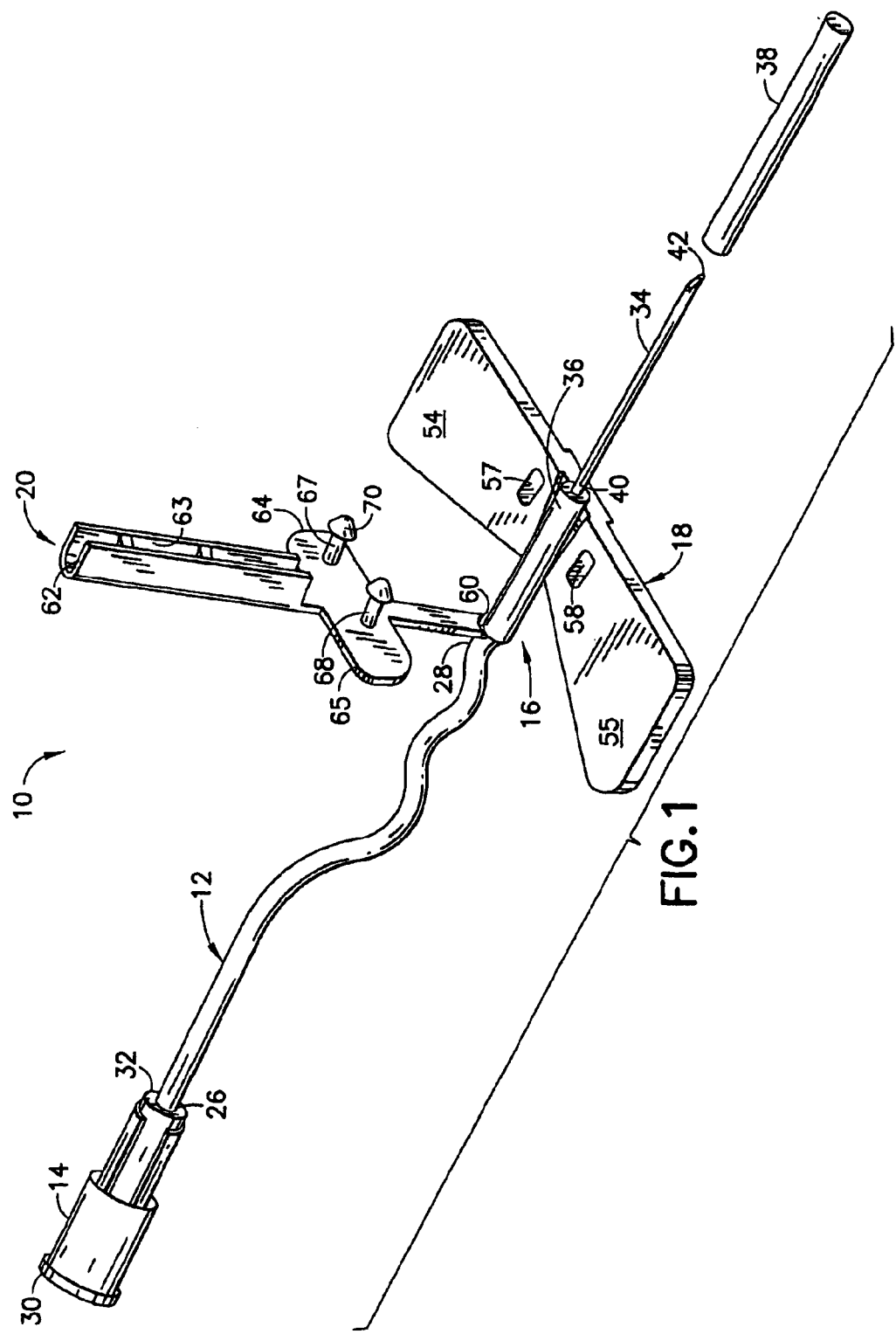
FIG. 1 is a perspective view of a first embodiment of the invention with the shield in the open position.
Figure 2:
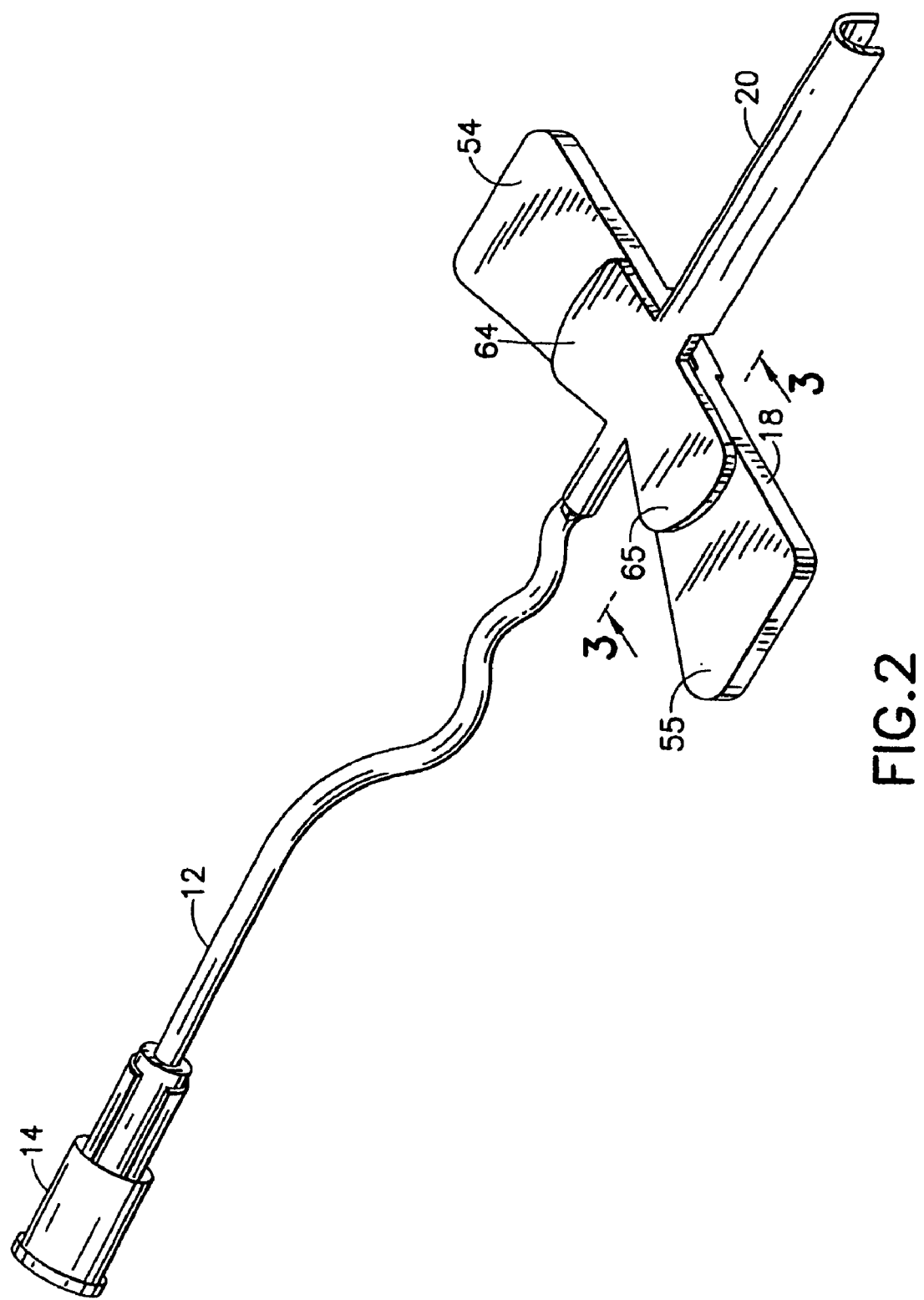
FIG. 2 is a perspective view similar to FIG. 1, but showing the shield in the closed position.
Figure 3:
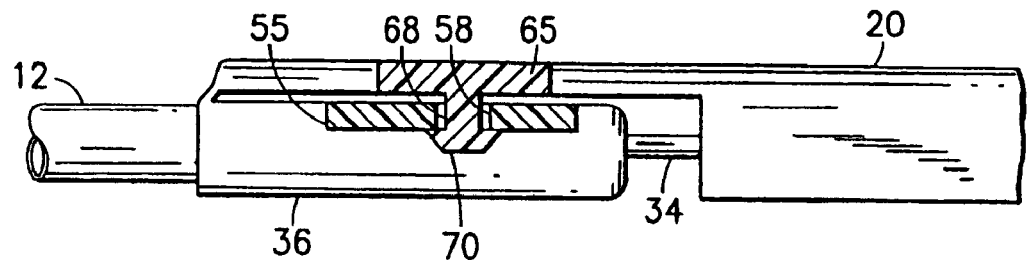
FIG. 3 is a cross-sectional view taken along line 3—3 in FIG. 2.

A first embodiment of a fluid collection/infusion set in accordance with the subject invention is identified generally by the numeral 10 in FIGS. 1–3. Fluid collection/infusion set 10 includes a length of flexible plastic tubing 12, a proximal fitting 14, a needle assembly 16, a winged grip 18 and a shield 20.

Tubing 12 includes a proximal end 26, a distal end 28 and a passage extending between the ends. Tubing 12 may be a conventional intravenous tubing used in conventional blood collection sets or infusion sets. Proximal connector 14 is molded unitarily from a plastic material and includes a proximal end 30, a distal end 32 and a passage extending between the ends. Portions of the passage adjacent distal end 32 are configured to telescope tightly over proximal end 26 of tubing 12 so that the passage through tubing 12 communicates with the passage through proximal connector 14. Adhesive, welding or the like can be employed to achieve a permanent connection between tubing 12 and proximal connector 14. Proximal end 30 of connector 14 defines a female Luer connector that can be mated with an appropriate male Luer connector. The male Luer connector may include a proximal needle cannula that can be placed in communication with an evacuated tube. Alternatively, a male Luer connector at the distal end of a conventional prior art syringe can be connected directly to proximal connector 14 for infusing a medication into the patient. In this instance, a separate male Luer cap can be provided for closing the proximal end of connector 14. Other fittings may be engaged threadedly with proximal connector 14 to achieve specific intended applications. Additionally, proximal connectors of other configurations may be employed to achieve a particular objective.

Needle assembly 16 includes a needle cannula 34, a needle hub 36 and a needle protector 38. Needle cannula 34 has a proximal end 40, a distal end 42 and a lumen 44 extending between the ends. Distal end 42 of needle cannula 34 is beveled to a sharp tip.

Needle hub 36 is molded unitarily from a plastic material such as polycarbonate, polypropylene, polyethylene, acrylic, polystyrene and ABS. Preferably needle hub 36 is molded from a transparent or translucent material to enable observation of blood or other fluid flowing through needle hub 36. Needle hub 36 includes a proximal end 46, a distal end 48 and a stepped passage (not shown) extending between the ends. Portions of the passage adjacent proximal end 46 are dimensioned to receive distal end 28 of tubing 12. More particularly, distal end 28 of tubing 12 is telescoped into the passage of needle hub 36 and is bonded in position adjacent proximal end 46 of needle hub 36. Portions of the passage adjacent distal end 48 of needle hub 36 are dimensioned for slidable receipt of proximal end 40 of needle cannula 34. More particularly, proximal end 40 of needle cannula 34 is secured permanently to needle hub 36 by epoxy and/or a mechanical affixation.

Needle protector 38 is a rigid cylindrical tube with a length that exceeds the projecting length of needle cannula 34 from needle hub 36. Needle protector 38 defines an inside diameter approximately equal to the outside diameter of the distal tip of needle hub 36. Thus, needle protector 38 can be telescoped over needle cannula 34 and frictionally retained on the distal tip of needle hub 36.

Winged grip 18 is molded from an elastic material such as polyolefin, polyvinyl chloride or other such elastomeric polymers. Winged grip 18 includes flexible wings 54 and 55 and a tubular mount. The tubular mount includes an interior passage that is dimensioned for snug engagement over needle hub 36. Wings 54 and 55 are formed respectively with locking apertures 57 and 58.

Safety shield 20 of the first embodiment has a proximal end 60, a distal end 62 and a generally U-shaped channel 63 extending from distal end 62 toward proximal end 60. Proximal end 60 of shield 20 is hinged to needle hub 36 at a location close to proximal end 46 of needle hub 36. More particularly, shield 20 may be molded unitarily with needle hub 36, and the hinged connection between shield 20 and needle hub 36 may define a living hinge at or near proximal end 60 of shield 20. Alternatively, proximal end 46 of needle hub 36 may define a hinge member that can be snapped into engagement with a mating hinge member at proximal end 60 of shield 20. Channel 63 of shield 20 is cross-sectionally dimensioned to receive needle cannula 34 therein. Additionally, distal end 62 of shield 20 is spaced from proximal end 60 by a distance that exceeds the distance between proximal end 46 of needle hub 36 and distal end 42 of needle cannula 34. Thus, shield 20 can be rotated from a first position, as shown in FIG. 1, where needle cannula 34 is fully exposed for use to a second position, as shown in FIG. 2 where needle cannula 34 is safely shielded.

Shield 20 includes structure for locking shield 20 in the second position substantially surrounding needle cannula 34. More particularly, as shown in FIG. 1, shield 20 is formed with tabs 64 and 65 that project transversely from proximal portions of shield 20. Tabs 64 and 65 define a large and conveniently located surface for receiving digital pressure to pivot shield 20 from the first position to the second position. Locking fingers 67 and 68 project rigidly from portions of tabs 64 and 65 that face wings 54 and 55. Locking finger 67, 68 includes locking detents 70, 71 at locations thereon spaced from tabs 64 and 65 by a distance substantially equal to the thickness of wings 54 and 55. Locking fingers 67 and 68 are disposed and dimensioned to pass through locking apertures 57 and 58 in wings 54 and 55. Wings 54 and 55 and locking fingers 67 and 68 will deform slightly in response to forces that move shield 20 into the second position around needle cannula 34. After sufficient rotation, locking detents 70 will pass entirely through locking apertures 57 and 58 in the respective wings 54 and 55. Wings 54 and 55 and locking fingers 67 and 68 then will resiliently return to an undeflected condition for securely locking shield 20 in the second position around needle cannula 34 and preventing reuse of needle cannula 34. Locking fingers 67 and 68 may be supplemental by cannula finger locks formed in channel 63 and configured for engaging cannula 34 when shield 20 is in the second position.

Figure 4:
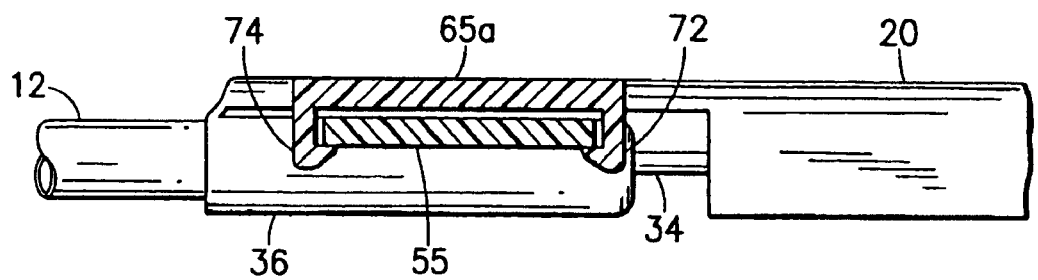
FIG. 4 is a cross-sectional view similar to FIG. 3, but showing a second embodiment.

The second embodiment of the needle assembly is illustrated in FIG. 4, and is structurally and functionally very similar to the first embodiment. Hence, comparable parts are provided with identical reference numerals, and a detailed description of the second embodiment is not provided. The second embodiment differs from the first embodiment in that wings 54 and 55 need not be provided with locking apertures. Additionally, tabs 64*a* and 65*a* are larger than tabs 64 and 65 in the first embodiment and have a proximal-distal dimension that exceeds the proximal-distal dimension of wings 54 and 55. Two locking fingers 72 and 74 project from tab 64*a* and are dimensioned to engage proximal and distal edges of wing 54*a*. Two identical locking fingers (not shown) project from wing 55. Thus, each wing 54, 55 is engaged at two locations for securely holding shield 20 in the second position surrounding needle cannula 34, as shown most clearly in FIG. 4. As in the first embodiment, wing locking fingers 72 and 74 can be supplemented by cannula locks.

Figure 5:
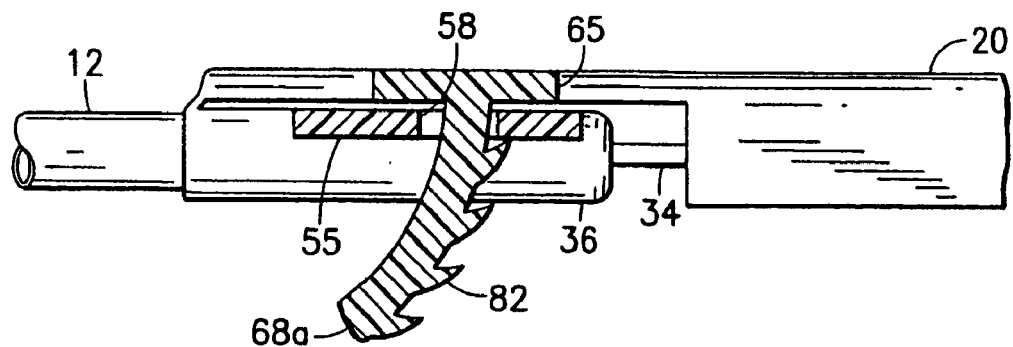
FIG. 5 is a cross-sectional view similar to FIGS. 3 and 4, but showing a third embodiment.

A third embodiment is illustrated in FIG. 5 and includes a needle cannula 34, a needle hub 36 and wings 54 and 55 substantially identical to the first embodiment. At least wing 54 is formed with locking aperture 58 as in the first embodiment. A shield 20 is hinged to needle hub 36 as in the first embodiment and can be rotated from a first position where needle cannula 34 is exposed to a second position where needle cannula 34 is shielded. A locking finger 68*b* projects from shield 20 and is received in locking aperture 56 of wing 54. Locking finger 68*b* is in the form of a ratchet, and thus differs from the locking fingers of the first two embodiments. More particularly, ratchet locking finger 68*b* extends rigidly from shield 20 through an arc substantially concentric with the axis of rotation of shield 20. Ratchet locking finger 68*b* is formed with a plurality of pawls 82, each of which is configured to slightly resist a forward movement of shield 20 and to prevent a return movement of shield 20 back toward the first position. Shield 20 will be retained in the second position by locked engagement of pawl 82 closest to shield 20 and may be retained further by a cannula finger lock.

Figure 6:
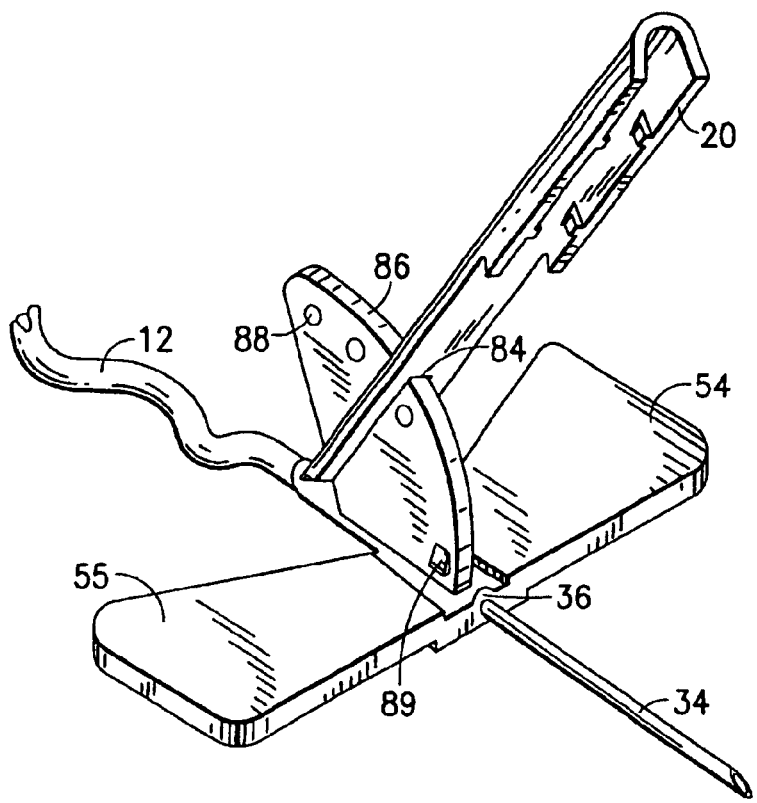
FIG. 6 is a perspective view of a safety needle assembly in accordance with a fourth embodiment.
Figure 7:
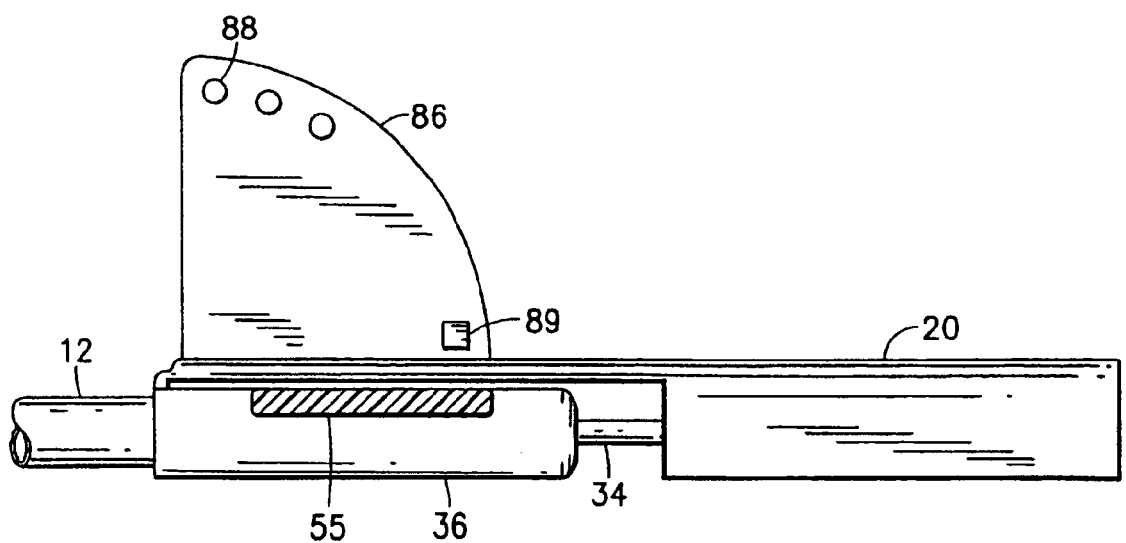
FIG. 7 is a cross-sectional view similar to FIGS. 3–5, but showing the embodiment of FIG. 6.

A fourth embodiment is illustrated in FIGS. 6 and 7, and includes a needle cannula 34, a needle hub 36 and wings 54 and 55, substantially as in the second embodiment. A shield 20 is hinged to needle hub 36 for rotation from a first position where needle cannula 34 is exposed to a second position where needle cannula 34 is shielded. Shield 20 includes a slot 84 that extends distally from the hinged connection to hub 36. A rigid dorsal fin 86 projects from needle hub 36 at a location equiangularly spaced from wings 54. Dorsal fin 86 is disposed to pass through slot 84 for all rotational movements of shield 20 from the first position to the second position. Dorsal fin 86 is formed with a plurality of detents disposed to engage portions of shield 20 on each side of slot 84 at each of a plurality of different rotational orientations of shield 20 relative to needle cannula 34 and needle hub 36. In particular, a first detent 88 is dimensioned and disposed to hold shield 20 releasably in the first position where shield 20 is rotationally spaced from needle cannula 34. A final detent 89 is disposed to permanently lock shield 20 in the second position surrounding needle cannula 34. One or more additional detents may be disposed between first detent 88 and the final detent 89. As in the previous embodiments, engagement of shield 20 with the detents on dorsal fin 72 can be supplemented by cannula finger locks formed within shield 20.

Figure 8:
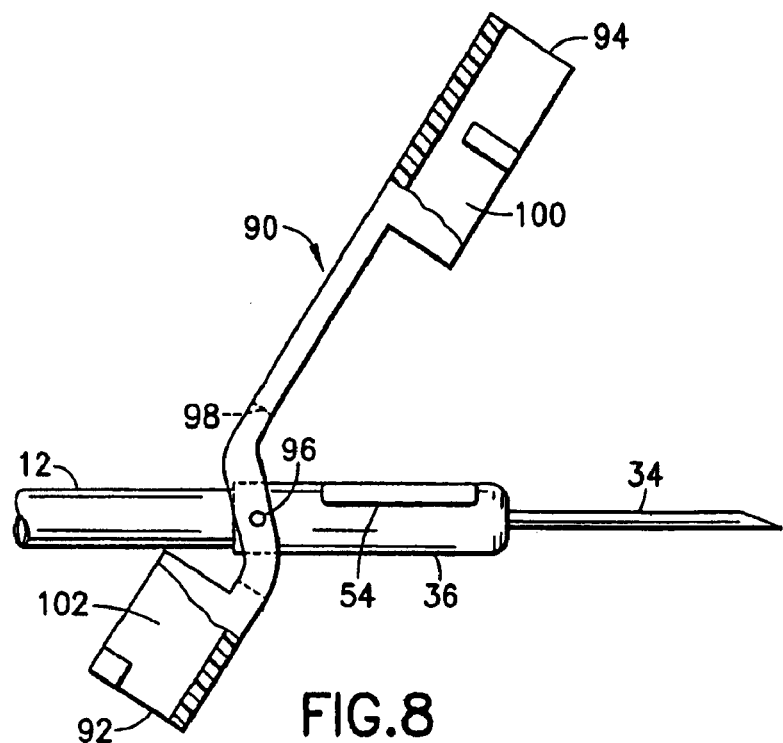
FIG. 8 is a side-elevational view partly in section of a safety needle assembly in accordance with a fifth embodiment of the invention.
Figure 9:
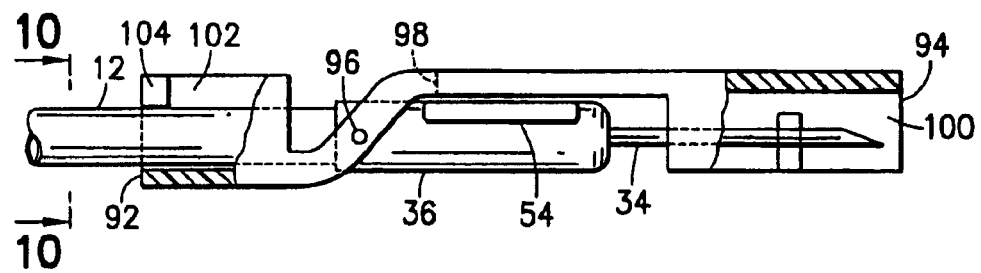
FIG. 9 is a view side-elevational of the assembly illustrated in FIG. 8, but showing the shield in the closed position.
Figure 10:
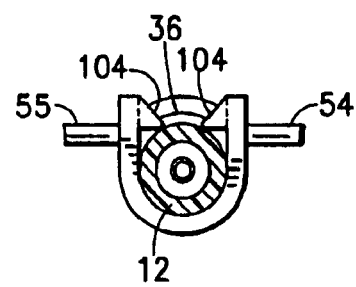
FIG. 10 is a cross-sectional view taken along line 10—10 in FIG. 9.

A fifth embodiment is illustrated in FIGS. 8–10, and includes a needle cannula 34, a needle hub 36, plastic tubing 12 extending from the proximal end of needle hub 36 and wings 54 and 55 projecting from needle hub 36 substantially as in the second embodiment. The safety needle assembly of FIGS. 8–10 further includes a shield 90 that is functionally similar to shield 20 described above and illustrated in FIGS. 1–7. In particular, shield 90 is hingedly connected to needle hub 36 and can be rotated from a first position where needle cannula 34 is exposed to a second position where needle cannula 34 is safely shielded. Shield 90, however, is structurally different from the preceding embodiments. In particular, shield 90 has a proximal end 92, a distal end 94 and a hinged connection 96 hingedly mounted to needle hub 36. Portions of shield 90 adjacent hinged connection 96 define a window 98 through which needle hub 36 extends. A channel 100 extends between window 96 and distal end 94 and opens in a direction for receiving needle cannula 34, substantially as in the preceding embodiments. Thus, the distance between hinged connection 96 and distal end 94 is sufficiently great to ensure complete shielding of needle cannula 34. Portions of shield 90 between window 98 and proximal end 92 define a channel 102 that is dimensioned to receive plastic tubing 12. Channel 102 is formed with a plurality of resilient deflectable tubing locks 104. Tubing locks 104 are dimensioned and configured to resiliently deflect in response to contact with flexible tubing 12. However, tubing locks 104 will return resiliently to an undeflected condition when shield 90 reaches the second position for preventing rotation of shield 90 back toward the first position. As in the other embodiments, shield 90 also may be provided with a cannula finger lock in channel 100 for securely and redundantly locking shield 90 in the second position.

Figure 11:
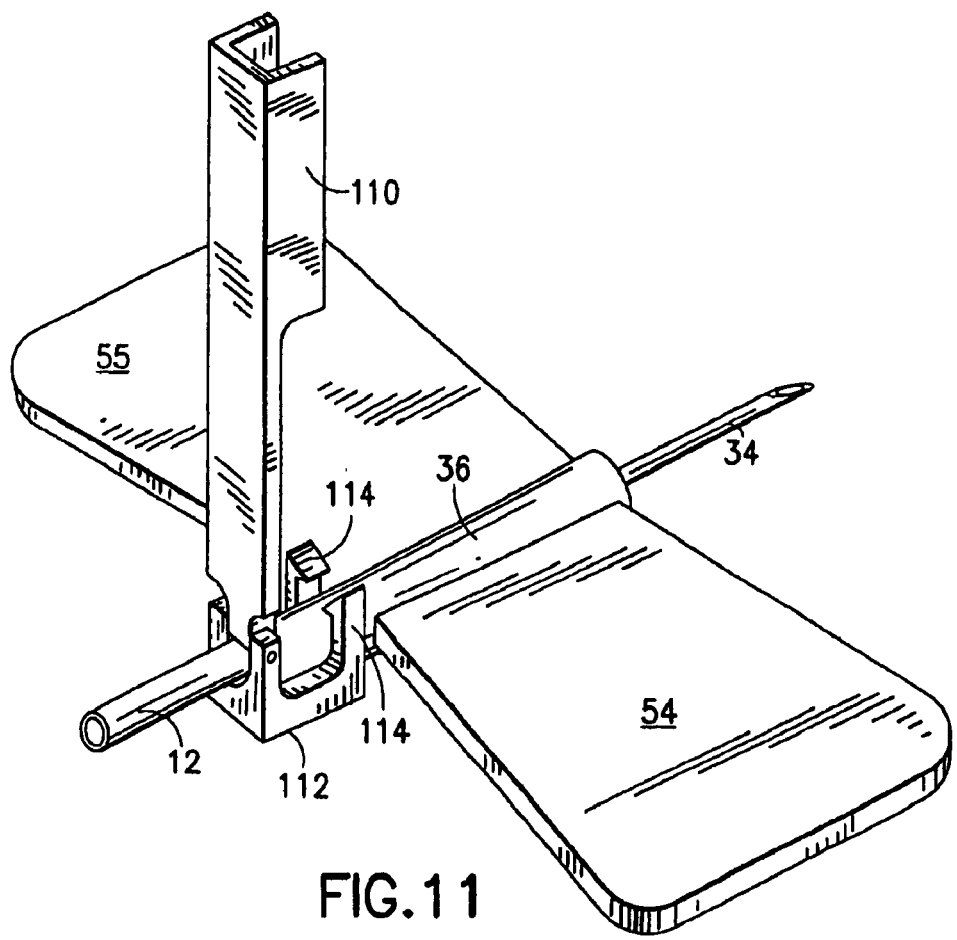
FIG. 11 is a perspective view of safety needle assembly in accordance with a sixth embodiment of the invention.
Figure 12:
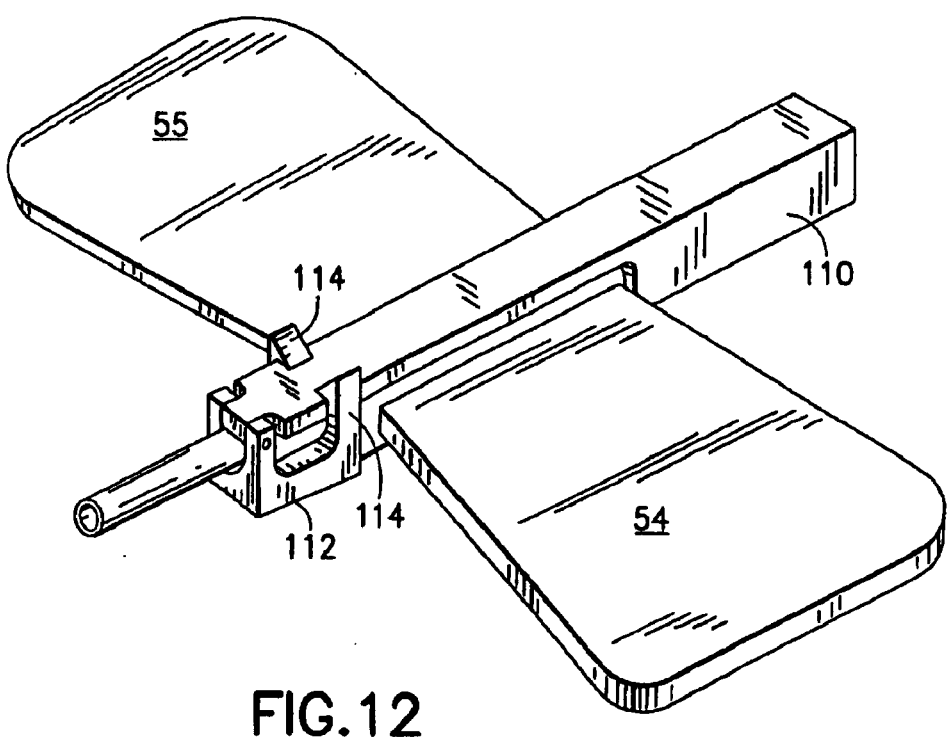
FIG. 12 is perspective view of the safety needle assembly shown in FIG. 11, but depicting the shield in the closed position.

A sixth embodiment is illustrated in FIGS. 11 and 12 and includes a needle cannula 34, a needle hub 36, and wings 54 and 55 projecting from needle hub 36, as in the other embodiments. A shield 110 is hinged relative to needle hub 36 for movement from a first position where needle cannula 34 is exposed to a second position where needle cannula 34 is shielded. However, shield 110 is not hinged directly to needle hub 36. Rather, shield 110 is hinged to a shield base 112 which in turn is securely mounted to proximal end 40 of needle hub 36. Shield base 112 is formed with a pair of opposed latches 114 disposed to lockingly engage shield 110 when shield 110 is rotated into the second position. Thus, shield 110 is part of a structure formed unitarily with shield base 112 and latches 114. Locking can be achieved entirely with structures on the unitarily formed shield 110 and shield base 112. Shield 110 may further include a cannula finger lock for redundantly locking shield 110 with needle cannula 34.

Figure 13:
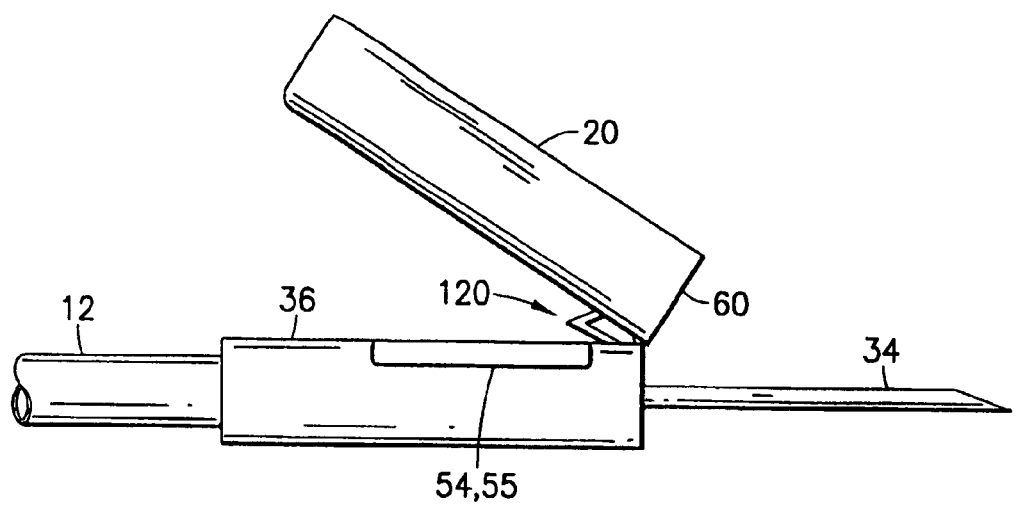
FIG. 13 is a side elevational view of a seventh embodiment of the safety needle assembly with the shield in an open position.
Figure 14:
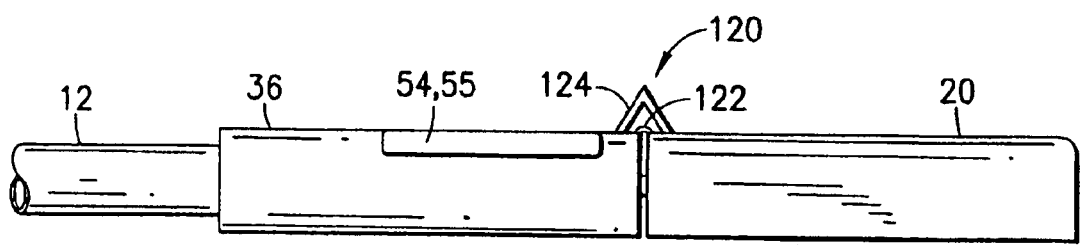
FIG. 14 is a side elevational view of the safety needle assembly shown in FIG. 13, but with the shield in the closed position.

Aspects of the invention described above pertain to the locking of the shield in the second position so that the needle is safely shielded. Other aspects of the invention pertain to structure for facilitating movement of the shield toward the second position. More particularly, a seventh embodiment of the invention is depicted in FIGS. 13 and 14, and includes a safety needle assembly having a needle cannula 34, a needle hub 36 and wings 54 and 55 substantially as in the preceding embodiments. A shield 20 is hingedly connected to needle hub 36. More particularly, proximal end 60 of shield 20 is connected unitarily to distal end 48 of needle hub 36 by an over center hinge identified generally by the numeral 120. Hinge 120 includes a primary hinge 122 and a plurality of articulated legs 124 connecting locations on hub 36 to locations on shield 20 spaced from primary hinge 122. Legs 124 are aligned to one another substantially at a right angle when shield 20 is in the first position of shield 20. Legs 124 are biased toward a straight angle as shield 20 is rotated about hinge 120 from the first position toward the second position. As shield 20 approaches the second position, legs 124 pass beyond a position of maximum extension and are biased back toward their original right angle disposition for accelerating shield 20 into the second position.

Figure 15:
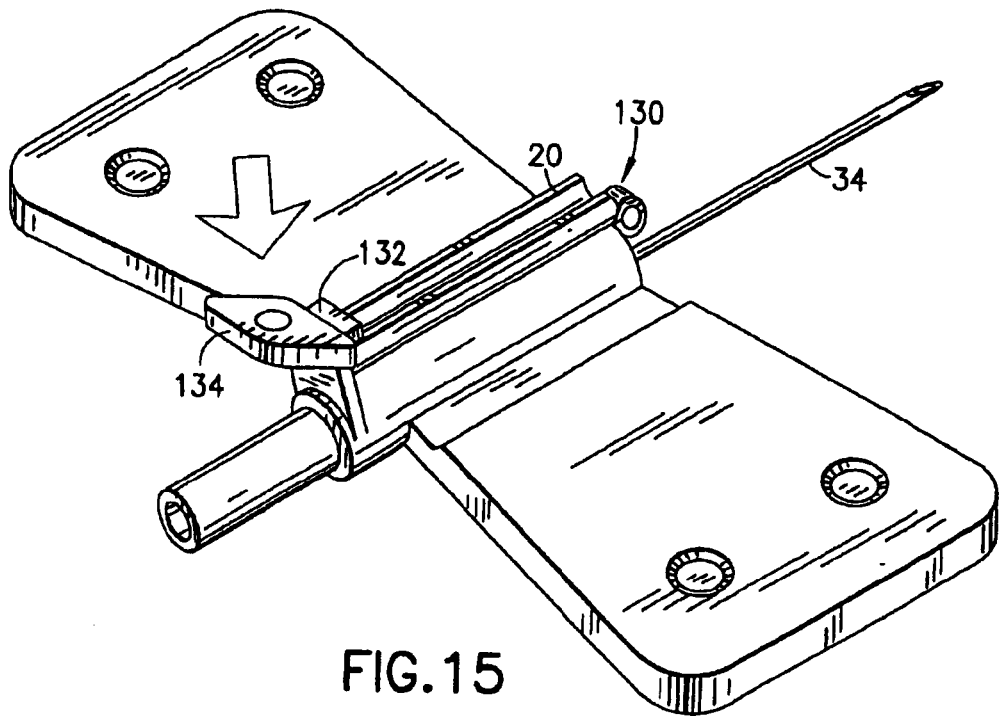
FIG. 15 is a perspective view of a safety needle assembly in accordance with an eighth embodiment of the invention with the shield in the open position.
Figure 16:
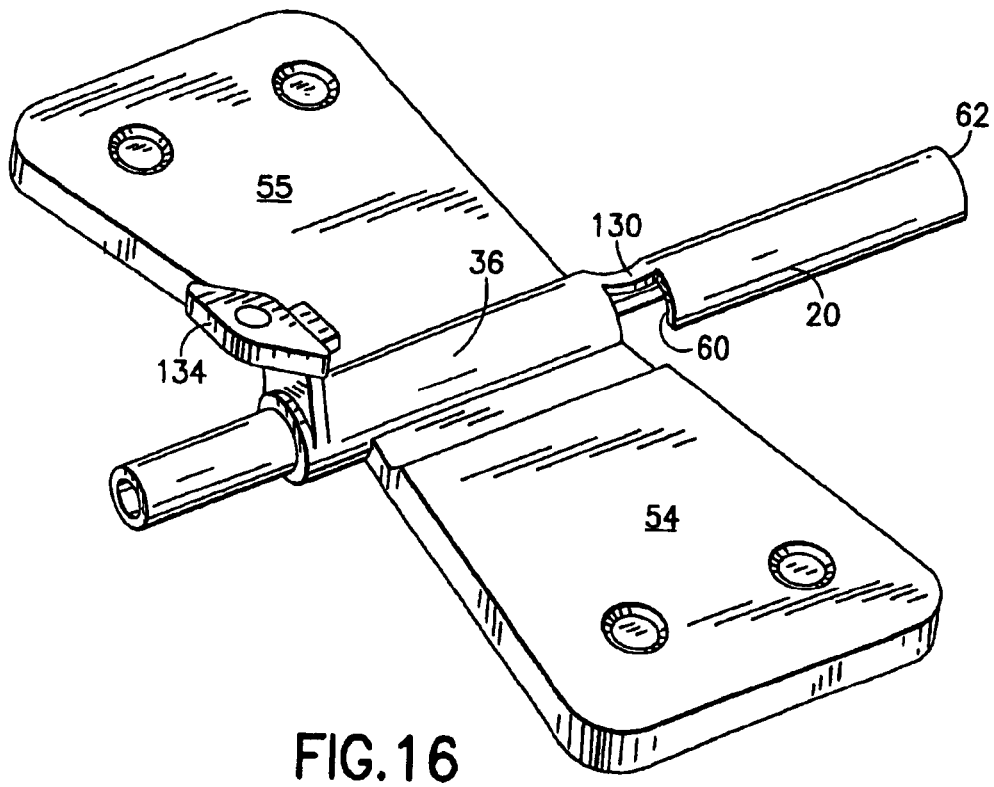
FIG. 16 is a perspective view of the safety needle assembly of the eighth embodiment, but showing the shield in the closed position.

An eighth embodiment is illustrated in FIGS. 15 and 16 and includes a needle cannula 34, a needle hub 36, and wings 54 and 55 substantially as in the preceding embodiments. The safety needle assembly of FIGS. 15 and 16 further includes a shield 20 with opposed proximal and distal ends 60 and 62. Proximal end 60 of shield 20 is joined unitarily to distal end 48 of hub 36 by a unitary hinge 130. Hinge 130 is biased into an orientation where shield 20 extends substantially linearly and distally beyond hub 36. However, hinge 130 permits shield 20 to be rotated approximately 180° in a proximal direction so that shield 20 substantially abuts hub 36 to define the first position of shield 20 relative to needle cannula 34 and hub 36.

Hub 36 further includes a shield latch 132 projecting from proximal end 46 of hub 36. Latch 132 is configured to engage distal end 62 of shield 20 when shield 20 is in the first position. An actuating lever 134 projects outwardly and proximally from shield latch 132. Actuating lever 134 can be depressed by a thumb or forefinger to deflect latch 132 sufficiently to disengage from shield 20. As a result, hinge 130 resiliently expands to the undeflected condition and propels shield 20 to the second position substantially surrounding needle cannula 34. As in the other embodiments, shield 20 is provided with at least one cannula finger latch for trapping cannula 34 and holding shield 20 in surrounding relationship to cannula 34.

Figure 17:
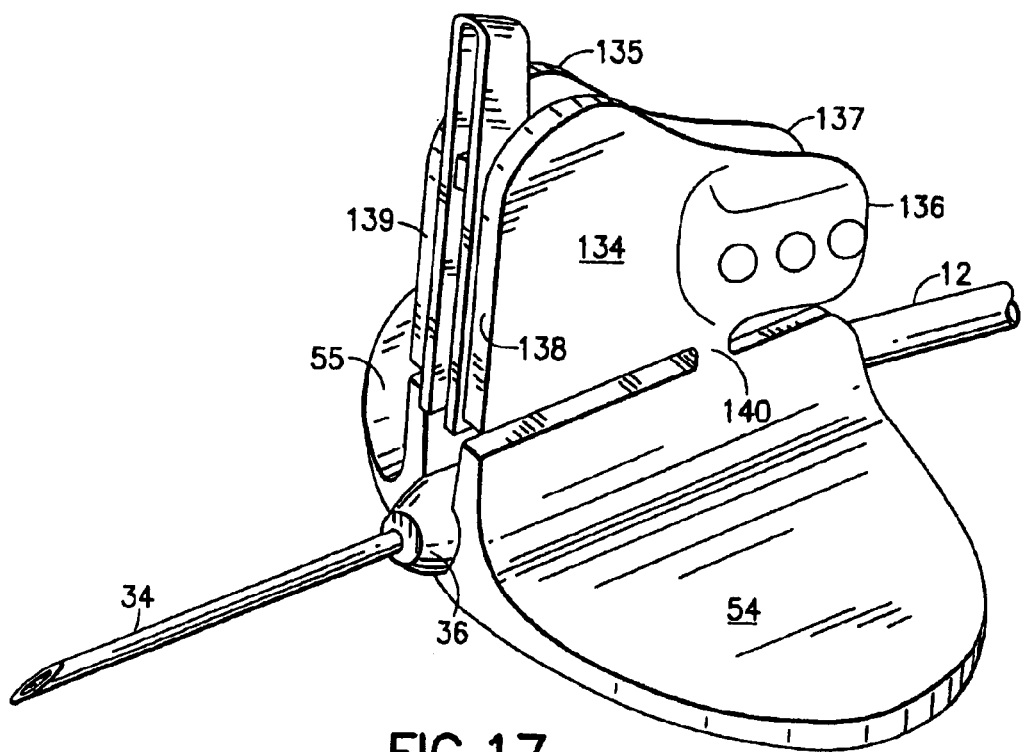
FIG. 17 is a perspective view of a safety needle assembly in accordance a ninth embodiment, with the shield in an open position.
Figure 18:
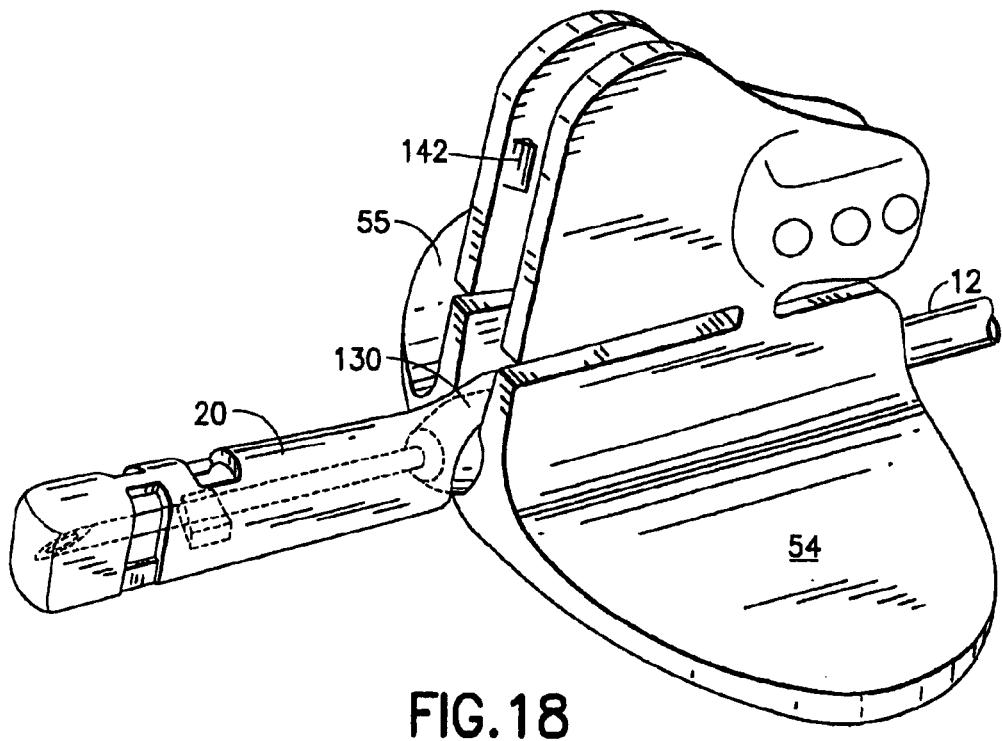
FIG. 18 is a perspective view similar to FIG. 17, but showing the shield in the closed position.

A ninth embodiment of the invention is illustrated in FIGS. 17 and 18, and is similar in several functional respects to the above-described eighth embodiment. More particularly, the ninth embodiment comprises a needle assembly with a needle cannula 34, a needle hub 36 and wings 54 and 55 as described above. Shield 20 is articulated to distal end 48 of hub 36 by a unitary hinge 130 that is biased to urge shield 20 into the second position substantially surrounding needle cannula 34. However, hinge 130 permits shield 20 to be rotated against the biasing forces of hinge 130 and into a first position where shield 20 is aligned substantially at a right angle to needle cannula 34, as shown in FIG. 15.

Dorsal fins 134 and 135 project up from the respective wings 54 and 55. Dorsal fin 134 and 135 have proximal ends 136 and 137, respectively, and distal ends 138 and 139, respectively. Dorsal fin 134 is connected to wing 54 at roots 140 disposed intermediate proximal and distal ends 136 and 138. A similar root (not shown) joins dorsal fin 135 to wing 55. Dorsal fins 134 and 135 are substantially parallel to one another and are spaced sufficiently for apart to permit shield 20 to be disposed between dorsal fins 134 and 135 when shield 20 is in the first position. Dorsal fins 134 and 135 further are formed with shield locks 142 on the opposed facing surfaces of dorsal fins 134 and 135. Locks 142 are disposed and configured to lockingly trap shield 20 and retain shield 20 in the first position.

The needle assembly of FIGS. 17 and 18 can be used by gripping opposed dorsal fins 134 and 135 at locations distal of root 140 for guiding needle cannula 34 into a targeted blood vessel or other source of bodily fluid. Needle cannula 34 is withdrawn from the patient after sufficient fluid has been collected or infused. Portions of dorsal fins 134 and 135 adjacent proximal ends 136 and 137 then are squeezed toward one another. This causes a pivoting of dorsal fins 134 and 135 about roots 140 so that distal ends 138 and 139 of dorsal fins 134 and 135 move further apart. As a result, shield latches 142 are disengaged from shield 20 and hinge 130 propels shield 20 into the second position. As in the other embodiments, cannula finger locks on shield 20 engage cannula 34 to lock shield 20 in the second position. Thus, shielding can be effected merely by shifting the location of gripping forces from a more distal position on dorsal fins 134, 135 to a more proximal position.

Figure 19:
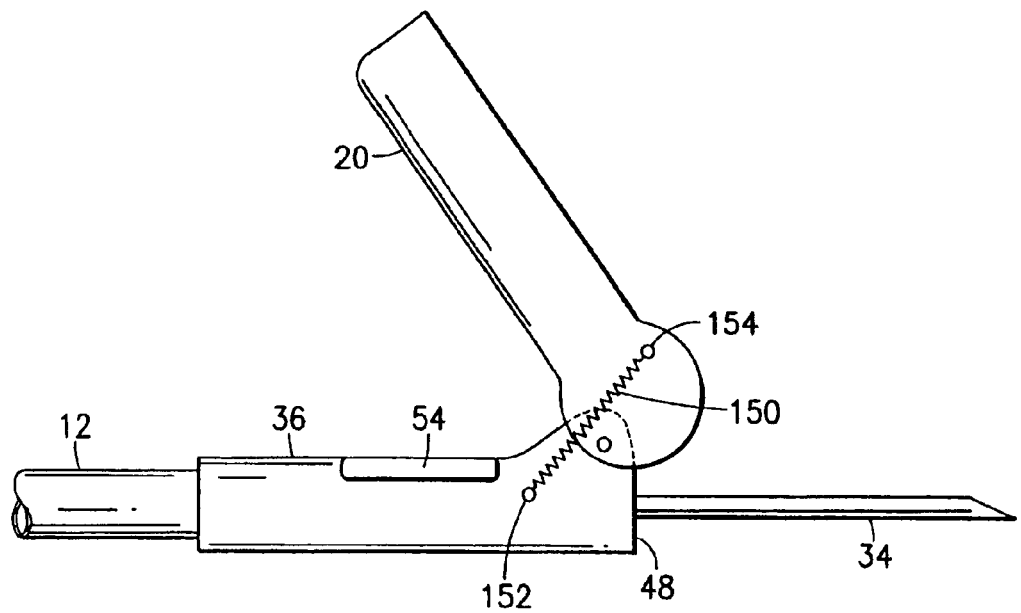
FIG. 19 is a side elevational view of a safety needle assembly in accordance with a tenth embodiment, with the shield in the open position.
Figure 20:
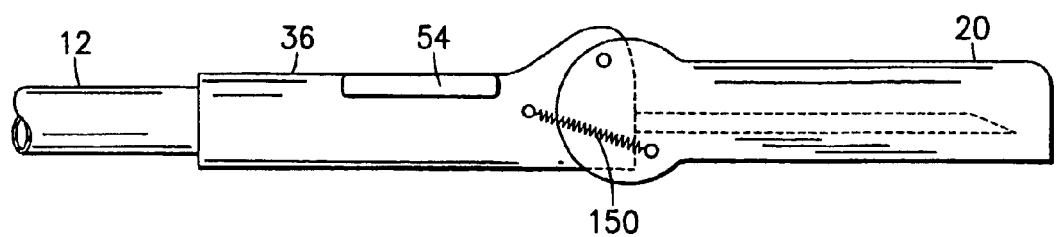
FIG. 20 is a side elevational view of the safety needle assembly shown in FIG. 19, but with the shield in the closed position.

The seventh through ninth embodiments achieved shielding assistance by the inherent biasing forces of a unitarily formed hinge. The tenth embodiment, however, employs a separate spring to facilitate shielding. More particularly, the tenth embodiment of the subject invention, as shown in FIGS. 19 and 20, relates to an assembly with needle cannula 34 and a needle hub 36. Needle hub 36 includes a distal end 48 from which needle cannula 34 extends. A shield 20 is hinged to needle hub 36 at a location near distal end 48 of shield 36. Shield 20 can be rotated from a first position where shield 20 is spaced from needle cannula 34 to a second position where shield 20 protectively surrounds needle cannula 34. The assembly further includes a spring 150 that functions much like over center legs 124 of the sixth embodiment and biased hinges 130 of the seventh and eighth embodiments. More particularly, spring 150 extends from hub 36 to shield 20. Spring 150 has a proximal end 152 connected to hub 36 and a distal end 154 connected to shield 20. Spring 150 is disposed to one side of the hinged connection between shield 20 and hub 36 when shield 20 is in the first position. Thus, spring 150 helps to hold shield 20 in the first position. Shield 20 can be moved manually from the first position toward the second position. This movement requires the user to overcome the forces exerted by spring 150. This movement also causes distal end 152 of spring 150 to move through an arc about the hinged connection between shield 20 and hub 36. After sufficient movement, spring 150 will move across the hinged connection between shield 70 and hub 36. At that point, spring 150 will begin assisting the movement of shield 20 toward the second position. Shield 20 is provided with cannula finger locks for locked engagement with needle cannula 34 when shield 20 reaches the second position.

Figure 21:
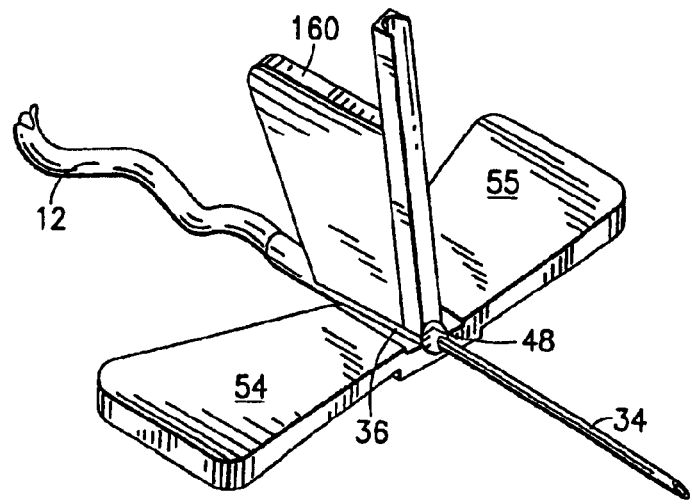
FIG. 21 is a perspective view of the safety needle assembly in accordance with an eleventh embodiment, with the shield in the open position.
Figure 22:
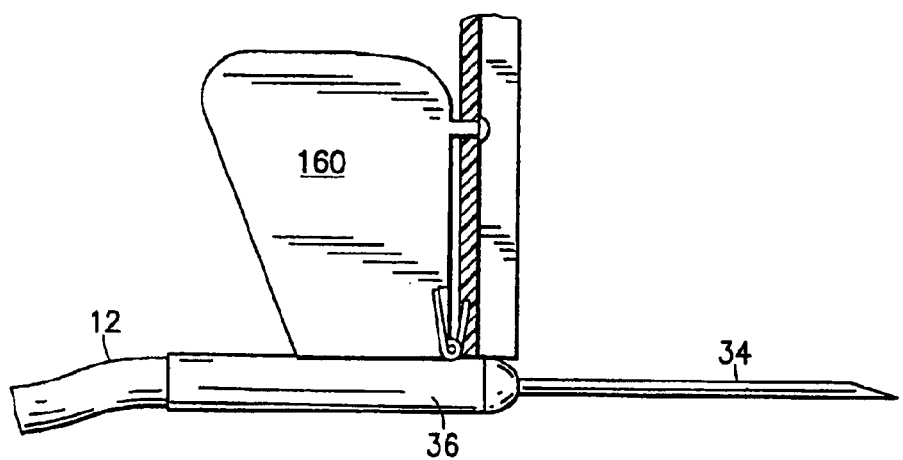
FIG. 22 is a side elevational view, partly in section, of the safety needle assembly shown in FIG. 21 with the shield in the open position.
Figure 23:
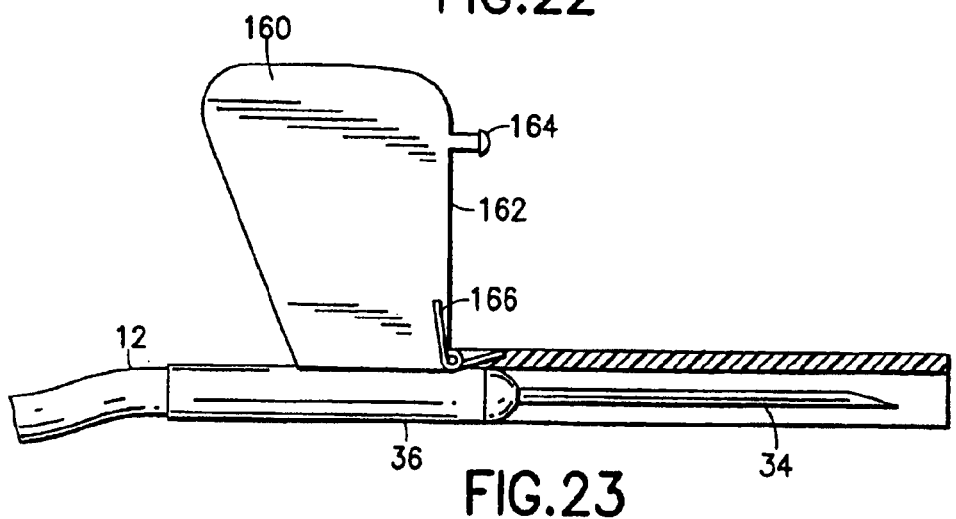
FIG. 23 is a side elevational view, partly in section, showing the safety needle assembly of FIGS. 21 and 22, but with the shield in the closed position.

The eleventh embodiment of the subject invention is illustrated in FIGS. 21–23 and employs a spring in a manner different from the tenth embodiment. More particularly, the eleventh embodiment includes needle 34, a needle hub 36 and wings 54 and 55. Needle hub 36 includes a distal end 48 and needle cannula 34 extends therefrom. A needle shield 20 is connected hingedly to distal end 48 of needle hub 36 and can move from a first position where needle cannula 34 is exposed to a second position where needle cannula 34 is shielded. A dorsal fin 160 projects substantially rigidly upwardly from hub 36 at a location equiangularly spaced between wings 54 and 55. Dorsal fin 160 includes a distal face 162 with a locking detent 164 projecting distally therefrom. Locking detent 164 is configured to lockingly engage shield 20 when shield 20 is in the first position. A torsional spring 166 is mounted adjacent distal end 48 of hub 36 and between distal face 162 of dorsal fin 160 and shield 20. Torsional spring 166 is collapsed and in a stored energy condition when shield 20 is engaged by locking detent 164.

The assembly of FIGS. 21–23 can be used substantially in the conventional manner by holding dorsal fin 160 and guiding needle cannula 34 into a targeted blood vessel. Upon completion of the medical procedure, the health care worker withdraws needle cannula 34 from the blood vessel and exerts a distal force on distal end 62 of shield 20. The force on shield 20 must be sufficient to overcome the holding forces of locking detent 164. Torsional spring 166 then releases its stored energy and propels shield 20 from the first position into the second position for safely surrounding needle cannula 34. Torsional spring 166 will continue to exert forces on shield 20 for holding shield 20 in its second position. However, more positive locked retention of shield 20 in the second position can be provided by a cannula finger lock as in the preceding embodiments.

Figure 24:
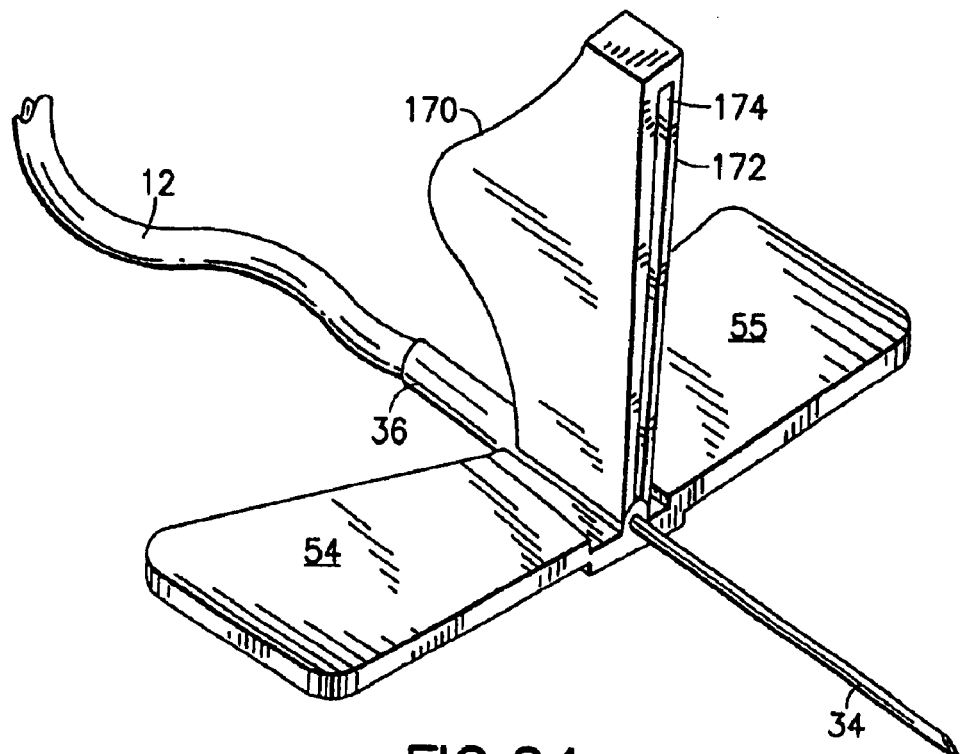
FIG. 24 is a perspective view of a safety needle assembly in accordance with a twelfth embodiment of the invention, and with the shield in the open position.
Figure 25:
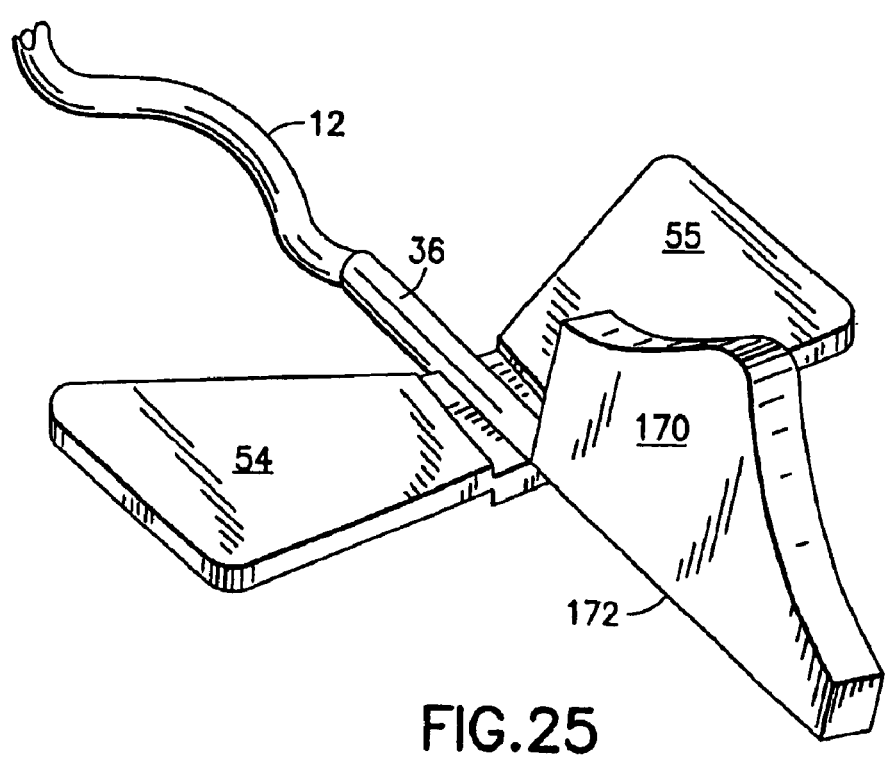
FIG. 25 is a perspective view of a safety needle assembly shown in FIG. 24, but with the shield in the closed position.

A twelfth embodiment of the subject invention is illustrated in FIGS. 24 and 25 and is similar to the eleventh embodiment. More particularly, the twelfth embodiment includes a needle 34 and a needle hub 36. Needle hub 36 includes a distal end 48 and needle cannula 34 extends therefrom. Wings 54 and 55 project transversely from hub 36. A needle shield 170 is hingedly connected to distal end 48 of needle hub 36. Needle shield 170 is in the form of a dorsal fin, and hence functions in a manner similar to the dorsal fin 160 of the eleventh embodiment illustrated in FIGS. 19–21 and described above. More particularly, shield 170 is a planar structure with a distal face 172 having an elongate groove 174 formed therein. Groove 174 is dimensioned and configured to receive needle cannula 34. The interior portions of groove 174 may include structure for locking needle cannula 34. For example, one or more cannula finger locks may be provided. Needle shield 170 further is provided with structure for releasable engagement of proximal portions of shield 170 with needle hub 36. The releasable engagement may be a locking detent similar to the locking detent 164 of the eleventh embodiment, latches similar to the latches 114 of the sixth embodiment illustrated in FIG. 10, an over center hinge construction similar to the seventh embodiment illustrated in FIGS. 11 and 12 or a frangible connection. With each of these optional constructions, needle cannula 34 can be used by manipulating shield 170 substantially in the same way as the manipulation of dorsal fin 160 of the eleventh embodiment. After use, needle cannula 34 is withdrawn from the patient. The health care worker then exerts a distal force on the proximal side of shield 170. As a result, the connection between shield 170 and needle hub 36 is separated, and shield 170 is propelled about the hinged connection to distal end 48 of needle hub 36 and into shielding engagement around needle cannula 34.

A thirteenth embodiment of the subject invention is illustrated in FIGS. 26–28 and includes a needle cannula 34 projecting from the needle hub 36. Wings 54 and 55 project transversely from needle hub 36. A shield 180 is hingedly connected to needle hub 36 and can be rotated from a first position where needle cannula 34 is exposed for use to a second position where shield 180 surrounds needle cannula 34. Shield 180 may be provided with structure for locked engagement with needle cannula 34, such as resiliently deflectable cannula locking fingers. Unlike the above-described embodiments, shield 180 is formed with a narrow longitudinal slot 182 on the side thereof opposite the elongate opening into which needle cannula 34 is received. Slot 182 may be substantially narrower than the needle-receiving opening of shield 180.

The assembly of FIGS. 26–28 further includes a hinged actuator 184. Actuator 184 has a proximal end 186 hingedly attached to hub 36 at a location proximally of the hinged connection of shield 36 to hub 34. Actuator 184 further includes a distal end 188. Portions of actuator 184 between proximal and distal ends 186 and 188 are slidably received in slot 182 of shield 180. Additionally, actuator 184 includes proximal and distal detents 190 and 192 that are spaced from one another by a distance slightly greater than the thickness of the plastic material from which shield 180 is formed. Distal detent 192 is snapped into slot 182 of shield 180 such that portions of actuator 184 between proximal and distal detents 190 and 192 are slidable in slot 182. With this construction, shield 180 can be rotated into a first position where needle cannula 34 is exposed for use. After use, distally directed forces can be exerted on actuator 184 by a thumb of the user of the device. These distally directed forces will cause actuator 184 to pivot around its proximal end 186. Simultaneously, proximal detents 190 will exert forces on the top wall of shield 180 adjacent slot 182 therein. Hence, shield 180 will pivot about needle hub 36 and into the second position surrounding needle cannula 34. Locking structures in shield 180 then will lockingly engage needle cannula 34.

Figure 29:
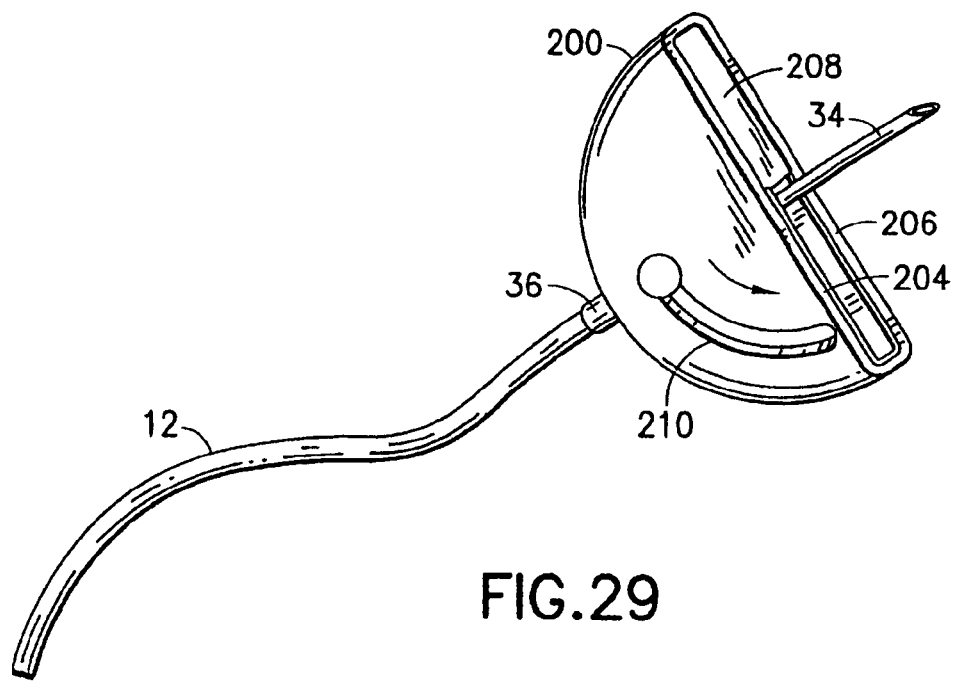
FIG. 29 is a perspective of a fourteenth embodiment of the invention with the shield in the open position.
Figure 30:
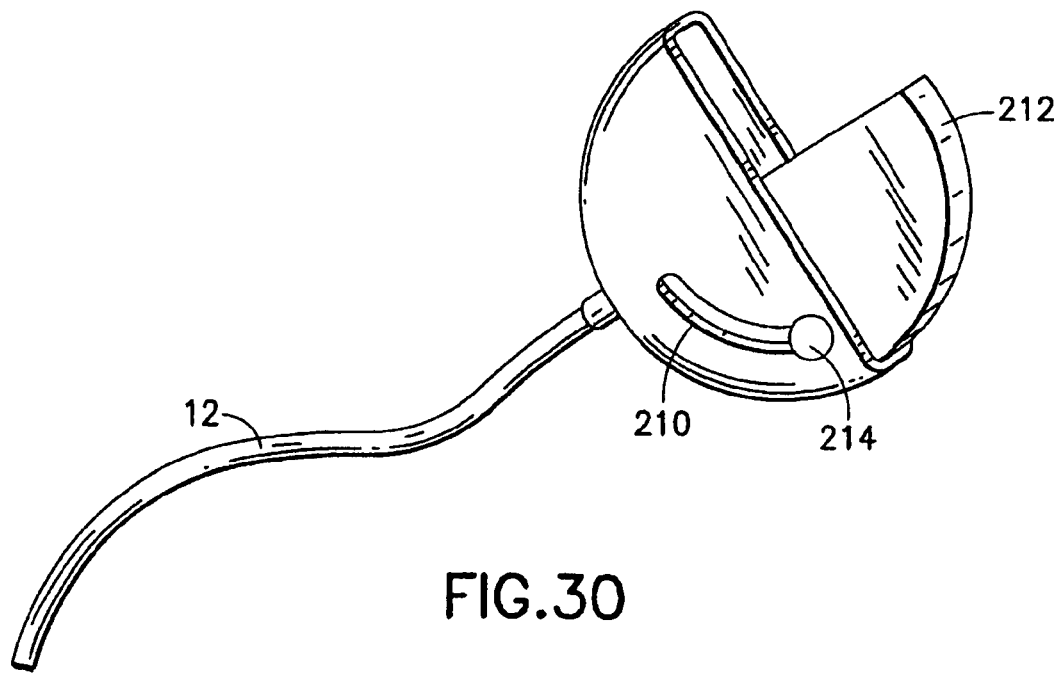
FIG. 30 is a perspective view of the safety needle assembly shown in FIG. 29, but with the shield in the close position.

The fourteenth embodiment of the subject invention is illustrated in FIGS. 29 and 30. The fourteenth embodiment includes a needle cannula 34 and a needle hub 36 substantially similar to a needle cannula and hub described with respect to the preceding embodiments. The fourteenth embodiment further includes wings 200 and 202 projecting transversely from opposite sides of hub 36. However, unlike the preceding embodiments, at least one wing 200 is substantially hollow and includes top and bottom walls 204 and 206 with a planar slot 208 extending distally between walls 204 and 206. Top wall 204 is formed with an arcuate slot 210 formed therethrough and extending through an arc generated about a location at or near the distal end of needle hub 36. A shield 212 is hingedly connected to hub 36 substantially at the center of rotation of arcuate slot 210 in top wall 204 of wing 200. Shield 212 includes an actuating projection 214 that extends through slot 210. The assembly shown in FIGS. 29 and 30 can be used substantially in a conventional manner by gripping wings 200 and 202 and inserting needle cannula 34 into the targeted blood vessel or other such source of bodily fluid. Upon completion of collection of fluid specimens, needle cannula 34 is withdrawn from the patient. The health care worker then moves actuating 214 of shield 212 through slot 210 in wing 200. As a result, shield 212 pivots about needle hub 36 sufficiently for shield 212 to substantially envelope and engage needle cannula 34.

What is claimed is:

1. A safety needle assembly comprising:
    a needle hub having opposite proximal and distal ends,
    a needle cannula having a proximal end connected to said distal end of said needle hub and a distal end projecting distally from said needle hub, wings projecting transversely from said hub,
    a needle shield hingedly connected to said needle hub and movable from a first position wherein said needle cannula is exposed and said needle shield is detached from said wings to a second position where said needle cannula is shielded by said needle shield, and
    a lock providing locked engagement between at least one of said wings and said shield when said shield is in said second position.

2. The safety needle assembly of claim 1, wherein the locked engagement substantially permanently locks said shield in said second position.

3. The safety needle assembly of claim 1, wherein, said lock comprises at least one finger projecting from said needle shield and configured for locked engagement with at least one of said wings.

4. The safety needle assembly of claim 3, wherein at least one of said wings includes a locking aperture formed therethrough, wherein said needle shield comprises said at least one locking finger, and wherein said at least one locking finger is configured for projecting through said locking aperture and lockingly engaging said wings when said shield is in said second position.

5. The safety needle assembly of claim 1,
    wherein each of said wings includes a locking aperture; and
    wherein said needle shield includes two locking fingers disposed for projecting through the locking apertures and lockingly engaging said wings when said needle shield is in said second position.

6. The safety needle assembly of claim 1, wherein the needle shield includes a substantially U-shaped channel dimensioned to receive said needle cannula therein when said shield is in said second position.

7. The safety needle assembly of claim 1, wherein said wings are formed from an elastic material.

8. The safety needle assembly of claim 7, wherein the wings are alignable to be in substantially coplanar relationship to one another.

9. The safety needle assembly of claim 1, wherein the wings are substantially parallel to the needle cannula.

10. The safety needle assembly of claim 1, wherein said wings are disposed in a substantially fixed position along said needle hub and relative to said needle cannula.

11. The safety needle assembly of claim 1 wherein said needle shield includes a proximal end hingedly connected to said hub, a distal end for shielding said needle cannula and an intermediate section between said proximal and distal sections for locking engagement with said wings.

12. The safety needle assembly of claim 1, wherein the needle shield is moveable by rotation from the first position to the second position.

* * * * *